United States Patent
Halleck et al.

[11] Patent Number: 6,147,618
[45] Date of Patent: Nov. 14, 2000

[54] APPARATUS AND METHOD FOR REDUCING POWER CONSUMPTION IN PHYSIOLOGICAL CONDITION MONITORS

[75] Inventors: Michael E. Halleck, Longmont; Michael D. Halleck, Northglenn, both of Colo.; Michael L. Lehrman, Washington, D.C.; Alan R. Owens, Longmont, Colo.

[73] Assignee: iLife Systems, Inc., Dallas, Tex.

[21] Appl. No.: 09/476,591

[22] Filed: Dec. 31, 1999

Related U.S. Application Data

[63] Continuation-in-part of application No. 09/396,991, Sep. 15, 1999.

[51] Int. Cl.⁷ .................................................. G08B 21/00
[52] U.S. Cl. .................... 340/669; 340/539; 340/825.36; 340/573.1; 340/554; 455/66; 455/41; 455/351; 455/343; 455/38.1
[58] Field of Search ..................................... 340/669, 539, 340/825.36, 573.1, 554; 455/66, 41, 351, 343, 38.1

[56] References Cited

U.S. PATENT DOCUMENTS 5,549,113  8/1996  Halleck et al. .......................... 128/671
6,011,477  1/2000  Teodorescu et al. ................. 340/573.1

*Primary Examiner*—Brent A. Swarthout
*Assistant Examiner*—Tai T. Nguyen

[57] ABSTRACT

There is disclosed an apparatus and method for reducing power consumption in physiological condition monitors that use a memory data storage device that operates in a high power mode when data is being written to the memory data storage device and operates in a low power mode when inactive. The apparatus comprises: 1) a controller for receiving incoming data to be written to the memory data storage device; and 2) a first low power buffer coupled to the controller. The controller stores the incoming data in the first low power buffer until a predetermined amount of incoming data has been accumulated in the first low power buffer and transfers the accumulated predetermined amount of incoming data to the memory data storage device in a single data transfer.

40 Claims, 11 Drawing Sheets

APPARATUS AND METHOD FOR REDUCING POWER CONSUMPTION IN PHYSIOLOGICAL CONDITION MONITORS

RELATED APPLICATIONS

This application is a continuation in part of co-pending U.S. patent application Ser. No. 09/396,991 filed Sep. 15, 1999 by Lehrman et al. entitled "Systems for Evaluating Movement of a Body and Methods of Operating the Same." A related patent application by M. D. Halleck has been filed concurrently with this patent application entitled "Apparatus and Method for Reducing Power Consumption in an Electronic Data Storage System" (Attorney Docket Number ILIF01-00004).

TECHNICAL FIELD OF THE INVENTION

The present invention is directed, in general, to systems for monitoring physiological conditions of a person and, more specifically, to systems that are capable of monitoring respiration waveforms, electrocardiogram (ECG) waveforms, blood oxygenation levels, blood glucose levels, movement and position orientation of a body, and other types of physiological information. The present invention is directed toward providing a significant reduction in the power consumption of physiological condition monitors. The present invention is especially useful in providing a significant reduction in the power consumption of battery operated flash memory data storage systems in physiological condition monitors.

BACKGROUND OF THE INVENTION

Specific types of physiological condition monitors are capable of monitoring specific types of physiological information. For example, one specific type of physiological condition monitor may be capable of monitoring a person's respiration activity. Other specific types of physiological condition monitors may be capable of monitoring cardiac activity, or blood oxygenation levels, or blood glucose levels, or movement of a body, or position orientation of a body, or other similar physiological conditions. A physiological condition monitor usually comprises one or more appropriate sensors coupled to the body of the person whose physiological conditions are to be measured.

In the case of sensors for detecting respiration activity or cardiac activity, the sensors are capable of sensing changes in pressure (or changes in other types of physical parameters) that are caused by the person's breathing and cardiac activity. Physiological condition monitors measure and record waveform signals received from the sensors. Electrocardiogram (ECG) waveform signals are the most commonly used waveforms for measuring a person's cardiac activity. Respiration waveform signals are used to measure a person's breathing rate and other types of information concerning respiration.

In the case of sensors for detecting blood oxygenation levels or blood glucose levels, the sensors are capable of sensing changes in the level of oxygen in the blood or changes in the level of glucose in the blood as those changes occur in the person's blood.

The present invention is capable of providing a significant reduction in the power consumption of any type of physiological condition monitor. For purposes of illustration, however, the present invention will first be described with reference to physiological condition monitors that are capable of monitoring respiration and cardiac activity. It is understood, however, that the present invention is not limited to use in respiration monitors or in cardiac activity monitors.

Low heart rate is referred to as bradycardia. Cessation of respiration is referred to as apnea. When a person exhibits apnea or bradycardia a life threatening condition very likely exists. Physiological condition monitors that are capable of continuously monitoring a person's respiration and cardiac activity are extremely useful for quickly detecting apnea or bradycardia. Such physiological condition monitors are also useful for quickly detecting other abnormal conditions such as a high heart rate (known as tachycardia) or a very slow breathing rate or a very high breathing rate.

Infants who are susceptible to sudden infant death syndrome are known to exhibit apnea and bradycardia. Physiological condition monitors that are capable of continually monitoring respiration and cardiac activity are particularly useful in the early detection of apnea or bradycardia in infants. Most physiological condition monitors are equipped with an alarm system to sound an alert when such conditions are detected.

A physiological condition monitor may be coupled directly to a person who is a patient in a hospital bed. In such an arrangement the waveform signals from the sensors coupled to the patient's body may be sent through wires directly to a detector circuit (and other circuitry) located in a console by the patient's bed. The wires attached to the patient restrict the patient's movements.

In other cases it is more practical to provide a physiological condition monitor located in a belt or harness that is to be worn by the person to be monitored. In this type of monitor the waveform signal information from the sensors is transmitted via a radio frequency transmitter to a radio frequency receiver in a base station unit that is located away from the site of the physiological condition monitor. The base station unit contains circuitry for analyzing and recording the waveform signal information. The base station unit contains circuitry for detecting abnormal conditions in the person's breathing or cardiac activity, such as apnea or bradycardia.

Because of the freedom of movement that this type of monitor provides, it is the preferred type of monitor for monitoring the physiological conditions of infants.

If the data that is acquired by the physiological condition monitor is not transmitted to the base station and recorded there, then the data must be recorded in a memory data storage device located within the physiological condition monitor. To preserve the freedom of movement that is provided by a belt or harness monitor, the memory data storage device within the physiological condition monitor must be battery powered.

One type of battery powered memory data storage device that can be used to record the data is a flash memory data storage system. As will be explained more fully below, the power requirements of prior art flash memory data storage systems have caused them to be inefficient in battery powered applications.

A physiological condition monitor that is capable of recording data in a memory storage device for over an extended period of time is very useful. By recording data over an extended period of time the physiological condition monitor can capture information concerning physiological events that do not occur regularly but occur only sporadically or rarely. A doctor or clinician can use the collected data to identify and evaluate such rare or sporadic physiological events.

For the data recording to have value it must recreate the physiological data in sufficiently fine detail to enable a doctor or clinician to identify and evaluate the physiological events represented by the data. This means that the physiological condition monitor must have a relatively high sampling rate throughout the period of time that the data is being recorded. This means that there will be a large amount of data to store.

There is a direct linear relationship between the amount of data to be stored and the quantity of energy needed to store it. To store a small amount of data requires a correspondingly small amount of electrical power. To store a large amount of data requires a correspondingly large amount of electrical power. In a battery powered memory data storage system in a physiological condition monitor, all of the electrical power must be provided by the battery. In order to collect and record the large amounts of data that are required, it is essential that the electrical power in the battery be conserved and used efficiently.

The present invention is directed toward providing a significant reduction in the power consumption of memory data storage systems used in physiological condition monitors. In particular, the present invention is directed toward providing a significant reduction in the power consumption of battery powered flash memory data storage systems used in physiological condition monitors.

A non-volatile data storage device is one that retains the data stored in it when external power to the device is shut off. One of the earliest non-volatile storage devices was punched paper tape. One of the most recent technologies for storing data in a non-volatile electronic data storage device is called "flash memory." Flash memory is a programable semiconductor memory of a type called "read-mostly" memory. Flash memory is so named because of the speed with which it can be reprogrammed. Flash memory uses an electrical erasing technology that can erase an entire flash memory array in a few seconds at most. Data written to flash memory remains in a non-volatile storage mode until the flash memory is deliberately erased. Flash memory requires a relatively high level of current (and a high level of electrical power to provide that current) when data is being written to the flash memory. A typical value of current required by flash memory when data is being written to the flash memory is sixty milliamps (60 mA).

CompactFlash™ memory is a relatively new flash memory data storage system. CompactFlash™ is a registered trademark of SanDisk Corporation. CompactFlash™ memory is very useful in various types of technological applications and represents a significant advance over other flash memory data storage systems for a number of reasons. In comparison with other flash memory data storage systems, CompactFlash™ memory has greater speed, greater durability, and smaller size. It is also packaged in a form that is very compatible with personal computers, especially laptop computers. CompactFlash™ memory makes it possible to store several tens of Megabytes of data on a memory card that is no larger than an ordinary matchbook. CompactFlash™ memory cards are now being used in digital cameras, in personal data assistants (PDAs), in MP3 audio players, and in other similar electronic data storage devices.

One of the drawbacks of CompactFlash™ memory (and of flash memory data storage systems in general) is that its operation requires a relatively high level of current. The greater the speed with which a flash memory data storage system is accessed, the more current it requires for operation. Even at the slowest access speeds, flash memory data storage systems generally require a comparatively large amount of current for operation.

For this reason flash memory data storage systems have not been widely used in battery powered devices for gathering electronic data. This is especially true for battery powered devices that acquire data slowly over a relatively long period of time. The power requirements of a flash memory data storage system in such a device would require continual and frequent replacement of the batteries. In many applications this requirement would make the use of a flash memory data storage system impractical.

It would be advantageous to have a flash memory data storage system in a physiological condition monitor in which the power consumption is reduced compared to the power consumption in prior art flash memory data storage systems. It would also be advantageous that any reduction of the power consumption in such a flash memory data storage system be achieved without a corresponding reduction in the performance level of the flash memory data storage system.

SUMMARY OF THE INVENTION

To address the deficiencies of prior art electronic data storage systems in physiological condition monitors, and especially those that require a relatively high level of current (and power) when data is being written to them, it is a primary object of the present invention to provide an improved electronic data storage system in a physiological condition monitor in which the power consumption of the electronic data storage system is reduced compared to the power consumption of prior art electronic data storage systems.

It is also an object of the present invention to provide an improved flash memory data storage system in a physiological condition monitor in which the power consumption of the flash memory data storage system is reduced compared to the power consumption in prior art flash memory data storage systems.

It is a further object of the present invention to provide an improved flash memory data storage system in a physiological condition monitor in which the reduction of the power consumption in the flash memory data storage system is achieved without a corresponding reduction in the performance level of the flash memory data storage system.

It is an additional object of the present invention to provide an improved flash memory data storage system for use in a battery powered device for gathering electronic data in a physiological condition monitor.

It is yet another object of the present invention to provide an improved flash memory data storage system for use in a battery powered device in a physiological condition monitor that acquires data slowly over a relatively long period of time.

Accordingly, in an advantageous embodiment of the present invention, there is provided, for use with a memory data storage device in a physiological condition monitor, where the memory data storage device operates in a high power mode when data is being written therein and operates in a low power mode when inactive, a system for minimizing a power consumption level of the memory data storage device comprising: 1) a controller capable of receiving incoming data to be written to the memory data storage device; and 2) a first low power buffer coupled to the controller, wherein the controller stores the incoming data in the first low power buffer until a predetermined amount of incoming data has been accumulated in the first low power buffer and wherein the controller transfers the accumulated predetermined amount of incoming data to the memory data storage device in a single data transfer.

In one embodiment of the present invention, the predetermined amount of incoming data is determined by a size of the predetermined amount of incoming data.

In another embodiment of the present invention, the size of the predetermined amount of incoming data is five hundred twelve bytes of data.

In still another embodiment of the present invention, the predetermined amount of incoming data is determined by a selected time duration during which the predetermined amount of incoming data has been accumulated.

In yet another embodiment of the present invention, the controller transfers the accumulated predetermined amount of incoming data to the memory data storage device when the memory data storage device is in the high power mode.

In a further embodiment of the present invention, the system further comprises a second low power buffer coupled to the controller capable of storing the incoming data when the accumulated predetermined amount of incoming data is being transferred from the first low power buffer to the memory data storage device.

In a still further embodiment of the present invention, the memory data storage device is of a battery powered type having a relatively high power consumption when data is written to the memory data storage device.

In a yet further embodiment of the present invention, the memory data storage device is a flash memory card.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the DETAILED DESCRIPTION OF THE INVENTION, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION

FIGS. 1 through 12, discussed below, and the various embodiments used to describe the principles of the present invention in this patent document are by way of illustration only and should not be construed in any way to limit the scope of the invention. Those skilled in the art will understand that the principles of the present invention may be implemented in a suitably modified physiological condition monitor.

Although the apparatus and method of the present invention can be utilized with any type of electronic data storage system in a physiological condition monitor, it is particularly useful in electronic data storage systems that require a relatively high level of current (and power) when data is being written to them. Although the present invention can be utilized with any type of electronic data storage system, the preferred embodiment of the present invention will be described in connection with a flash memory data storage system. The particular flash memory data storage system that will be described is known as CompactFlash™ memory.

Figure 1:
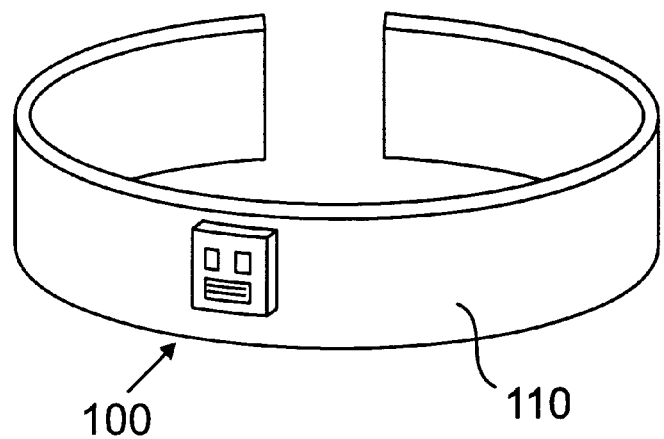
FIG. 1 is a perspective view of the monitor unit of the physiological condition monitor of the present invention.

FIG. 1 is a perspective view of an advantageous embodiment of monitor unit 100 of the physiological condition monitor of the present invention. Monitor unit 100 contains physiological condition sensors (not shown) that are capable of being coupled to the body of the person whose physiological conditions are to be monitored. Monitor unit 100 may be mounted on belt 110 which is capable of being worn by the person whose physiological conditions are to be monitored. As will be explained more fully below, monitor unit 100 contains a flash memory data storage system for storing the physiological condition data collected by the physiological condition sensors within monitor unit 100.

Figure 2:
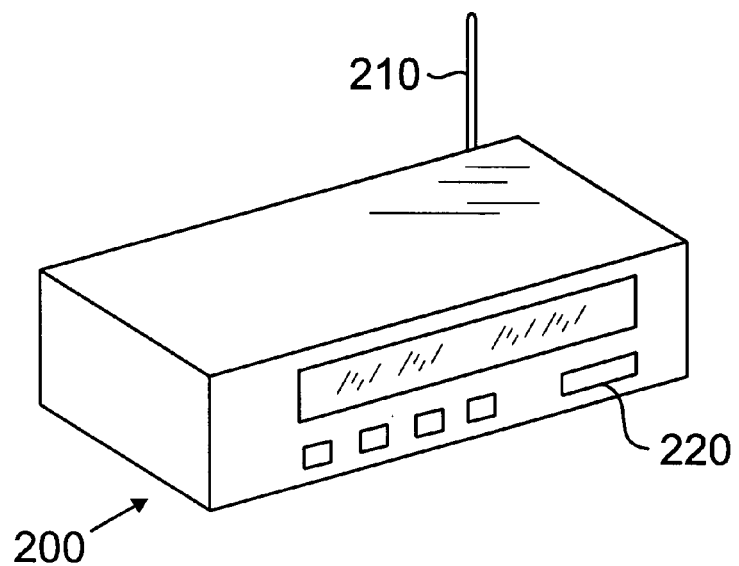
FIG. 2 is a perspective view of the base station unit of the physiological condition monitor of the present invention.

FIG. 2 is a perspective view of base station unit 200 of the physiological condition monitor of the present invention. Base station unit 200 has a radio frequency receiver (not shown) which is capable of receiving radio frequency transmissions via antenna 210. As will be described more fully below, in one advantageous embodiment of the present invention, monitor unit 100 contains a radio frequency transmitter for sending physiological condition data to base station 200.

Base station 200 also contains a PCMCIA slot 220 for receiving a flash memory card. In one advantageous embodiment of the present invention, a flash memory card that contains recorded data may be physically removed from monitor unit 100 and placed in the PCMCIA slot 220 of base station 200. Base station 200 can then access and display the data that is stored in the flash memory card.

Figure 3:
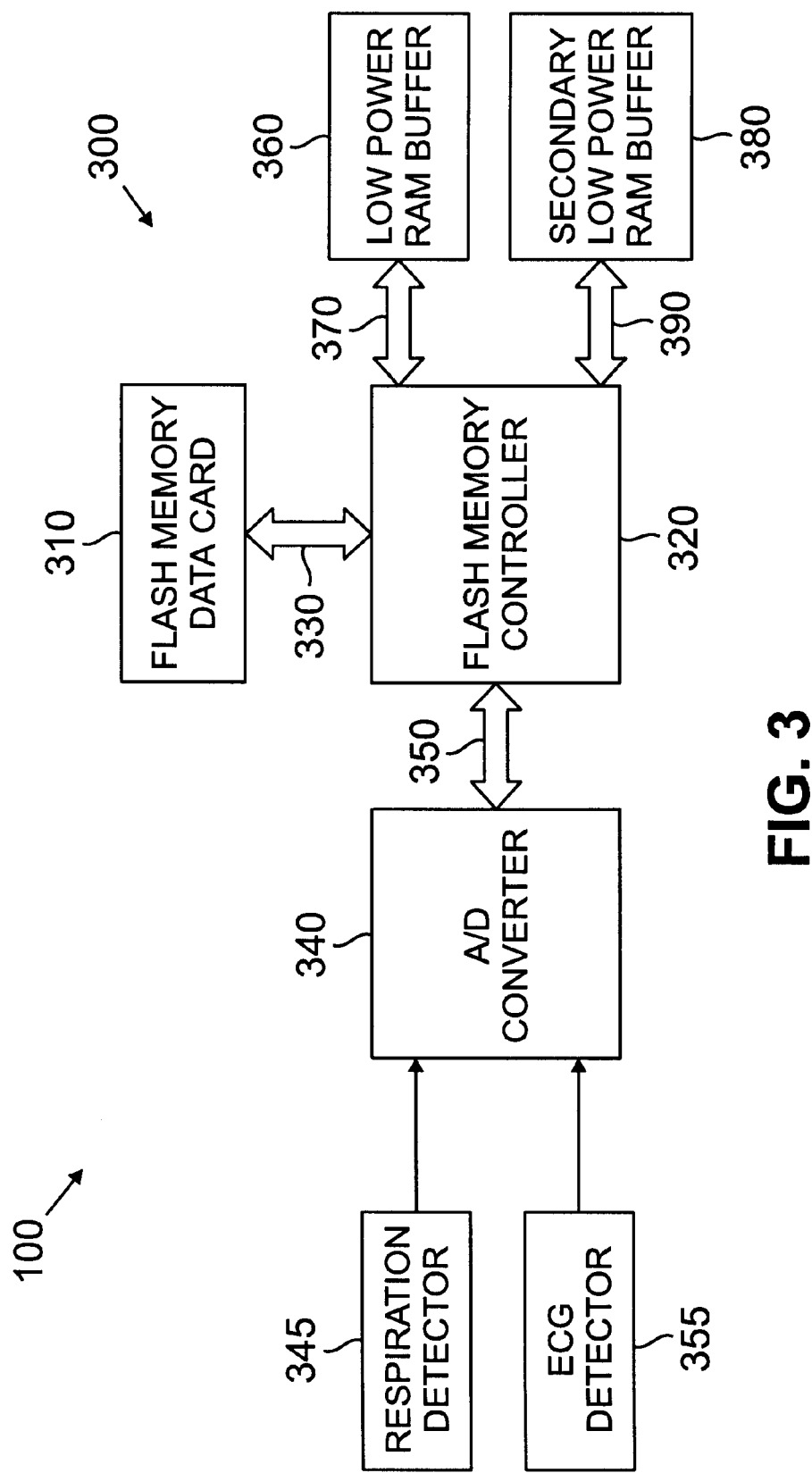
FIG. 3 is a block diagram of one embodiment of the monitor unit of the present invention showing the interconnection of the components of a flash memory data storage system utilizing the present invention.

FIG. 3 is a block diagram of one embodiment of monitor unit 100 of the present invention showing the interconnection of the components of flash memory data storage system 300 embodying the present invention. Flash memory data storage system 300 comprises flash memory data card 310. In an advantageous embodiment of the invention, flash memory data card 310 is a CompactFlash™ data card. However, other types of flash memory data cards 310 may be used. A battery (not shown) provides the power to operate the components of monitor unit 100.

Flash memory data card 310 is coupled to controller 320 through interface 330. Controller 320 is a data processing circuit that may read and write data to and from flash memory data card 310. Controller 320 is also coupled to data acquisition unit 340 through interface 350. Data acquisition unit 340 receives external data from respiration detector 345 and electrocardiograph (ECG) detector 355. Data acquisition unit 340 may also receive external data from other input devices or other types of physiological condition detectors (not shown).

Respiration detector 345 and electrocardiograph detector 355 comprise sensors and electronic signal amplifier circuitry of the type disclosed in U.S. Pat. No. 5,549,113 to Halleck et al. entitled "Apparatus and Method for Remote Monitoring of Physiological Parameters," which is incorporated herein for all purposes.

Data acquisition unit 340 sends data to controller 320 for ultimate transfer to and storage in flash memory data card 310. Data acquisition unit 340 may be, for example, a multiplexer, an analog-to-digital converter (ADC), an input/output (I/O) data buffer, a digital data channel, or the like. In the embodiment of the present invention shown in FIG. 3, data acquisition unit 340 is an analog to digital converter (ADC).

Controller 320 is also coupled to a low power RAM buffer 360 through interface 370. Low power RAM buffer 360 is used to temporarily store data from controller 320. As will be described in detail, low power RAM buffer 360 accumulates data from controller 320 and then sends the accumulated data through controller 320 to flash memory data card 310 under the control and direction of controller 320.

As previously mentioned, in an advantageous embodiment of the invention flash memory data card 310 is a CompactFlash™ data card, which is a non-volatile electronic data storage device that can store several tens of Megabytes of mass storage data. It is compatible with the PC Card ATA protocol and is also True IDE Mode compatible. It also is capable of a "low power" (or "sleep") mode of operation in which the data card temporarily ceases to use full power and draws only a relatively small amount of current. It also presently has one of the smallest form factors (i.e., module size) in the industry.

CompactFlash™ data cards are generally considered to be low power devices. This is certainly true when CompactFlash™ data card is compared to a mechanical hard disk drive. However, a CompactFlash™ data card may still have an unacceptably large power consumption when it is used in battery powered devices. This is especially so when the battery powered devices are designed to use small size batteries. When a CompactFlash™ data card is active, it uses sixty milliamps (60 mA) of current when data is being written. To supply this much current during a period of continuous operation of a CompactFlash™ data card, it would be necessary to provide the electrical power of approximately one (1) double-A (AA) alkaline battery per day. Therefore, to supply power to a battery powered flash memory data storage system for continuous data acquisition one would have to provide the electrical power of approximately seven (7) double-A (AA) alkaline batteries to operate the system for one (1) week.

As will be shown, flash memory data storage system 300 and the method of the present invention provides a significant power reduction for battery operated flash memory data storage systems. The power reduction provided by the present invention enables flash memory data card 310 described above to be continuously operated for more than eleven (11) days on just a single (i.e., only one) double-A (AA) alkaline battery. This represents more than a ten to one (10 to 1) improvement in the performance of flash memory data card 310 for the same level of power expended (i.e., one (1) double-A (AA) alkaline battery).

One may also express the improved performance in terms of power reduction. That is, for the same level of performance, the present invention requires approximately one tenth (0.10) of the power or approximately ten percent (10%) of the power that would otherwise be required in a prior art flash memory data storage system.

The power requirements of flash memory data card 310 are related to one of its most powerful and useful features, the ATA protocol interface. The ATA protocol interface allows a computer system (whether a personal computer, laptop, personal digital assistant (PDA), or the like) to treat flash memory data card 310 as if it were a mechanical hard disk drive. That is, the ATA protocol interface of flash memory data card 310 allows it to emulate a mechanical hard disk drive. To install flash memory data card 310 into a computer, the user simply inserts flash memory data card 310 into the PCMCIA slot in the computer (using, for example, a CompactFlash™ to PCMCIA adapter). Then the user can access data on flash memory data card 310 as easily as accessing the local hard disk drive of the computer.

Unfortunately, the ATA protocol interface imposes some restrictions in the interface that make the slow acquisition of data expensive in terms of power consumption. The primary restriction is the requirement that data be written to flash memory data card 310 in blocks of five hundred twelve (512) bytes at a time. That is, data cannot be written to flash memory data card 310 in increments of less than 512 bytes. Flash memory data card 310 must remain in high power mode for the entire time that the 512 bytes are being sent. Flash memory data card 310 can enter its low power (or sleep) mode of operation only after an entire 512 byte block has been received.

Figure 7:
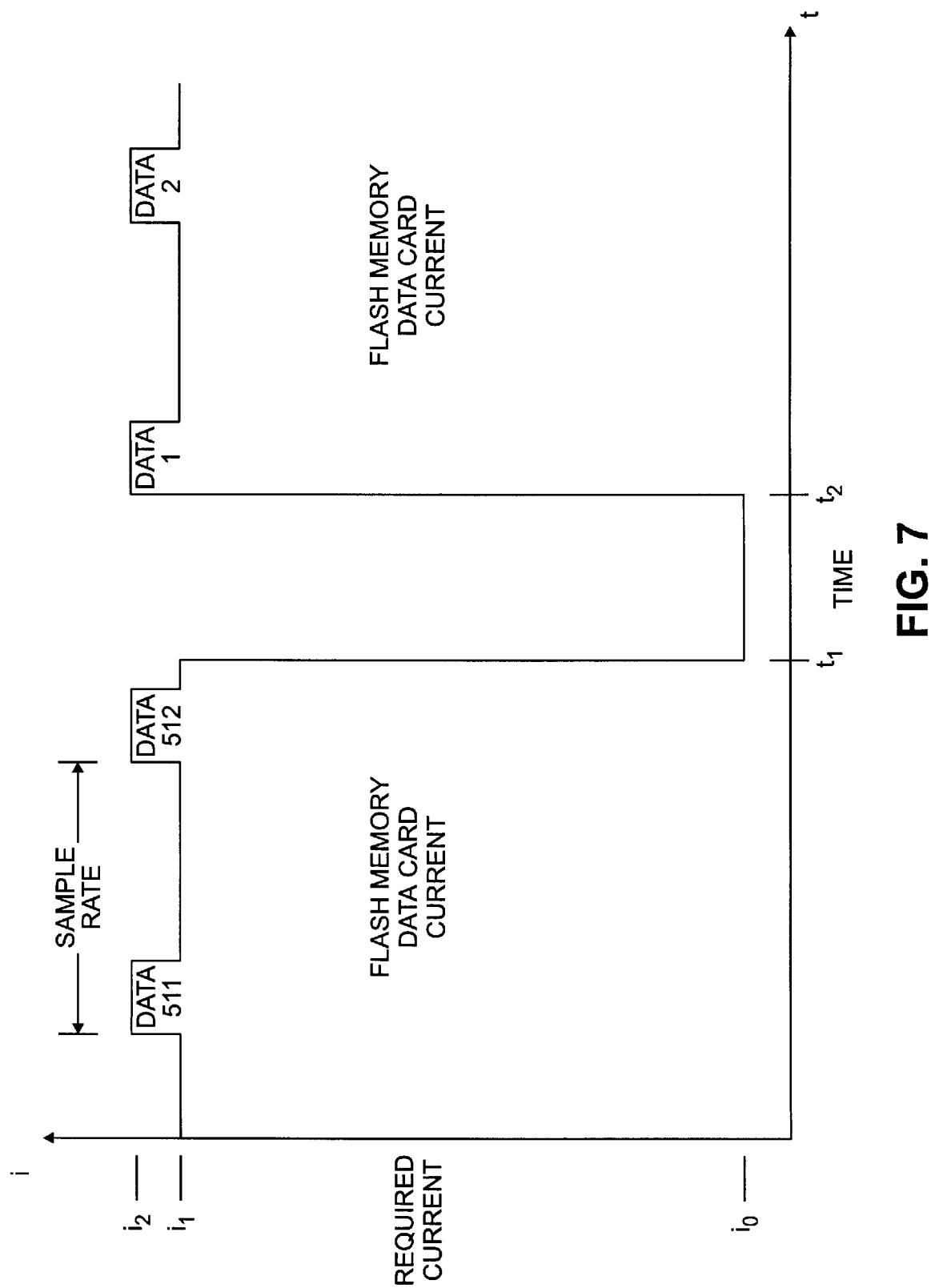
FIG. 7 is a data timing diagram showing the current required by a flash memory data card during a typical sequence for acquiring and writing data in a flash memory data card not utilizing the present invention.

A result of this feature is that a flash memory data card 310 that does not employ the apparatus and method of the present invention spends a relatively large amount of time in full power mode waiting for data, particularly if data is received slowly. This may be seen by referring to FIG. 7. FIG. 7 is a data timing diagram showing the current required by flash memory data card 310 during a typical sequence in which data is slowly acquired and written to flash memory data card 310. Flash memory data card 310 draws full power during the entire time that it is waiting for the 512 bytes of data. This power level is represented in FIG. 7 by a current having a value of $i_1$. When a byte of data, such as data byte 511 or data byte 512 is being written to flash memory data card 310, a little extra power is required for a short time. This is represented in FIG. 7 by a current level having a value of $i_2$. Between the acquisition of each of the individual bytes of data, flash memory data card 310 draws a current with a value of $i_1$. As flash memory data card 310 receives a block of data one byte at a time, from Byte 1 up to Byte 512, the required current fluctuates between the values of $i_1$ and $i_2$.

As shown in FIG. 7, the sample rate time is the length of time from the beginning of one byte of data to the beginning of the next byte of data. The sample rate time may be relatively long compared to the length of time it takes to acquire one byte of data. Flash memory data card 310 must continue to wait during the entire sample rate time during data acquisition. In doing so, flash memory data card 310 continues to draw full power even though it is effectively doing nothing but waiting for data.

After flash memory data card 310 has received and written the last byte in a block of data (i.e., the $512^{th}$ byte), flash memory data card 310 stores the block of data and goes into its low power mode of operation. This happens at time $t_1$ as shown in FIG. 7. In the low power mode of operation, flash memory data card 310 draws a very small amount of current. This low power level is represented in FIG. 7 by a very small amount of current having a value of $i_0$.

As soon as the next data is written, flash memory data card 310 again begins to draw full power. This happens at time $t_2$ as shown in FIG. 7. The time that flash memory data card 310 is in low power mode is equal to the time $t_2$ minus the time $t_1$, a time that is less than the sample rate time. Therefore, flash memory data card 310 is in low power mode only during every $512^{th}$ sample. This equates to two tenths percent (0.2%) of the time. Flash memory data card 310 draws full power ninety nine and eight tenths percent (99.8%) of the time.

In order to conserve power, the present invention utilizes low power RAM buffer 360. As controller 320 receives data from data acquisition unit 340 through interface 350, controller 320 writes the data to low power RAM buffer 360 through interface 370, instead of writing the data to flash memory data card 310. While low power RAM buffer 360 is accumulating the data, flash memory data card 310 is in its low power mode of operation. After the low power RAM buffer 360 has accumulated one 512-byte block of data, controller 320 causes flash memory data card 310 to terminate low power (or sleep) mode and to return to full power mode to receive the data. Controller 320 then transfers the 512-byte data block from low power RAM buffer 360 to flash memory data card 310. This method ensures that flash memory data card 310 is only in its high power mode during the time that the accumulated block of data is being transferred from low power RAM buffer 360 to flash memory data card 310.

Figure 8:
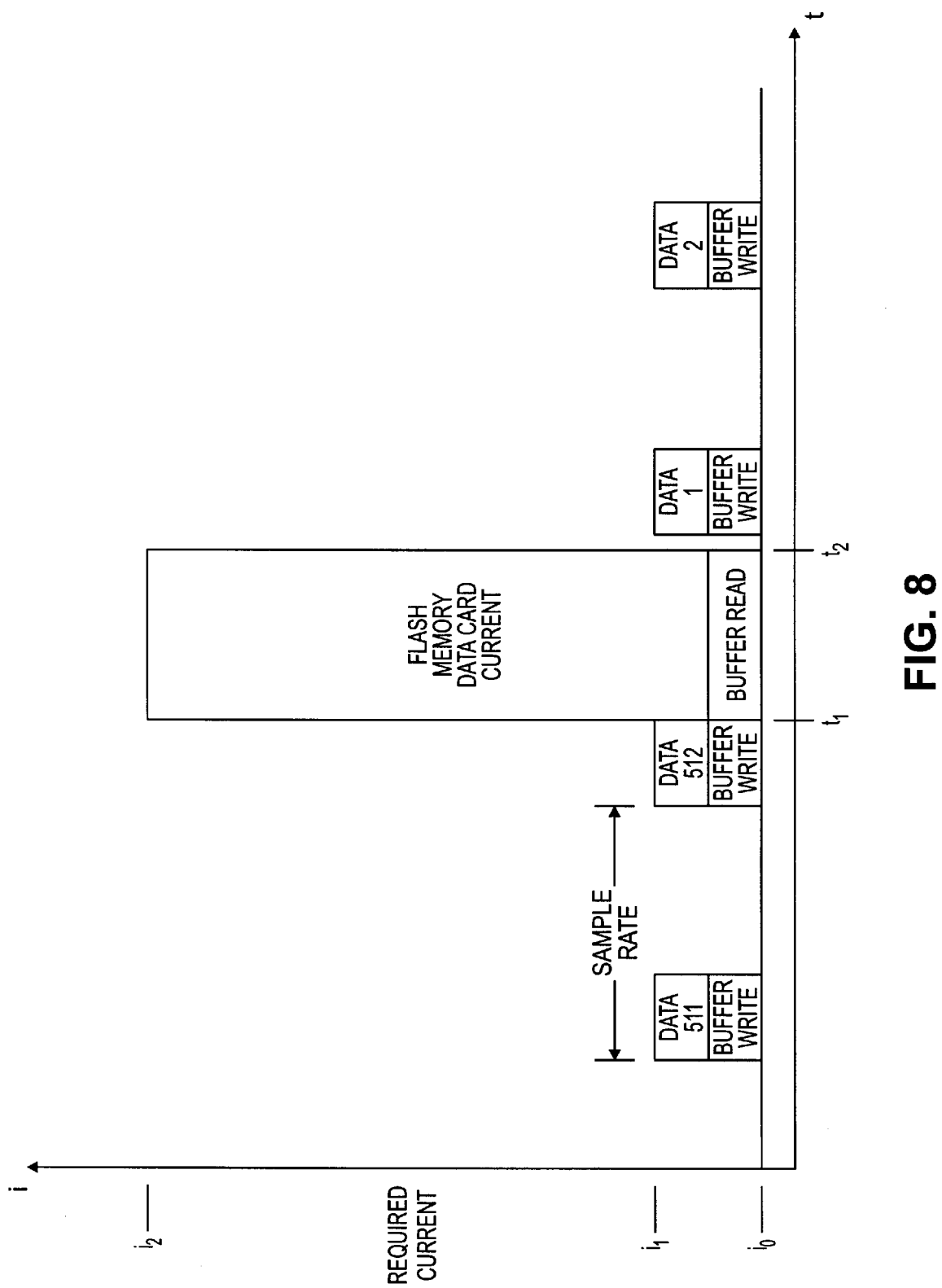
FIG. 8 is a data timing diagram showing the current required by a flash memory data card during a typical sequence for acquiring and writing data in a flash memory data card that utilizes the present invention.

The present invention enables flash memory data card 310 to spend a relatively short amount of time in full power mode while it is receiving data. This may be seen by referring to FIG. 8. FIG. 8 is a data timing diagram showing the current required by flash memory data card 310 during a typical sequence for acquiring and writing data in accordance with the apparatus and method of the present invention. Flash memory data card 310 draws full power only during the time that it is receiving data from low power RAM buffer 360. This power level is represented in FIG. 8 by a current having a value of $i_2$. While flash memory data card 310 is waiting for low power RAM buffer 360 to accumulate a block of data, flash memory data card 310 is in low power mode of operation. As previously mentioned, in the low power operation, flash memory data card 310 draws a very small amount of current. This very small amount of current is part of the quiescent system current that is represented in FIG. 8 by a current having a value of $i_0$.

The amount of current required for flash memory data storage system 300 to acquire and write one byte of data in low power RAM buffer 360 is represented in FIG. 8 by a current having a value of $i_1$. Between the individual acquisition of each of the individual bytes of data, flash memory data storage system 300 draws a current with a value of $i_0$, the quiescent system current. As low power RAM buffer 360 receives a block of data one byte at a time, from Byte 1 up to Byte 512, the required current fluctuates between the values of $i_0$ and $i_1$.

Because flash memory data card 310 is in low power mode while low power RAM buffer 360 is acquiring a block of 512 bytes of data, a relatively long sample rate time has no negative effect on the amount of current required to operate flash memory data storage system 300. In the previously described prior art embodiment, the operating current was at an increased level during the entire sample rate time, however long the sample rate time happened to be.

After low power RAM buffer 360 has received and written in its buffer the last byte in a block of data (i.e., the $512^{th}$ byte), controller 320 causes flash memory data card 310 to exit low power mode and transfers the block of data from low power RAM buffer 360 to flash memory data card 310. This happens at time $t_1$ as shown in FIG. 8. In this active mode of operation, flash memory data card 310 draws a relatively large amount of current. This high power level is represented in FIG. 8 by a current having a value of $i_2$.

After flash memory data card 310 has read and stored all of the block of 512 bytes of data, controller 320 causes flash memory data card 310 to return to low power mode. This happens at time $t_2$ as shown in FIG. 8. The time that flash memory data card 310 is at its full power level is equal to the time $t_2$ minus the time $t_1$. If the sample rate is sufficiently slow (i.e., if the time between the samples is sufficiently long) the situation will be that as shown in FIG. 8. In FIG. 8 flash memory data card 310 has received all of the block of 512 bytes of data from low power RAM buffer 360 and has returned to low power mode before the arrival of Byte 1 of the next block of data. In this situation, flash memory data card 310 is in low power mode during 511 out of every 512 samples. This equates to ninety nine and eight tenths percent (99.8%) of the time. Flash memory data card 310 is drawing full power only during two tenths of a percent (0.2%) of the time. This represents a complete reversal of the situation that existed in the case of the previously described prior art embodiment.

It takes a fixed amount of time to transfer the accumulated block of data out of low power RAM buffer 360 to flash memory data card 310. In cases where the sample rate is sufficiently fast (i.e., where the time between the samples is sufficiently short) it will be necessary for flash memory data storage system 300 to continue to acquire data during the time of the data transfer from low power RAM buffer 360 to flash memory data card 310.

To meet this requirement secondary low power RAM buffer 380 is coupled to controller 320 through interface 390 to acquire the data from data acquisition unit 340 that is being transferred through interface 350 to controller 320 during the time that the previously accumulated block of 512 bytes of data is being transferred from low power RAM buffer 360 to flash memory data card 310. After low power RAM buffer 360 has completed the task of transferring the most recently accumulated block of data to flash memory data card 310, the contents of secondary low power RAM buffer 380 are transferred through interface 390 and through controller 320 and through interface 370 to low power RAM buffer 360. The data collection then continues in accordance with its normal operation. Low power RAM buffer 360 may sometimes be referred to as the "primary" low power RAM buffer 360 to distinguish it from secondary low power RAM buffer 380.

It is possible that controller 320 may receive data from data acquisition unit 340 during the time that secondary low power RAM buffer 380 is transferring data to primary low power RAM buffer 360. If this happens controller 320 interrupts the transfer and stores the data in secondary low power RAM buffer 380. Controller 320 then causes the transfer to resume. This process may repeated if necessary. When the transfer is completed controller 320 causes the stored data to be transferred to low power RAM buffer 360 in its sequential order.

The storage capacity of secondary low power RAM buffer 380 must be large enough to hold all data that is acquired from controller 320 during the time that primary low power RAM buffer 360 is transferring the most recently accumulated block of data to flash memory data card 310. The storage capacity that will be needed by secondary low power RAM buffer 380 for most applications will typically be less than the storage capacity of primary low power RAM buffer 360. However, the storage capacity of secondary low power RAM buffer 380 may be larger than the storage capacity of primary low power RAM buffer if so required for a particular application.

Controller 320 handles all the interface/bus timing signals between flash memory data card 310 and low power RAM buffer 360 and secondary low power RAM buffer 380 and data acquisition unit 340. Controller 320 may be implemented as a microprocessor or a programmable logic device or a similar type of electronic control circuit.

If controller 320 is a microprocessor, low power RAM buffer 360 and secondary low power RAM buffer 380 may be subcomponents of the microprocessor. For ATA protocol interface applications a minimum storage capacity of five hundred twelve (512) bytes is required for low power RAM buffer 360. For other types of applications the minimum storage capacity of low power RAM buffer 360 may be greater than or less than five hundred twelve (512) bytes of data. Low power RAM buffer 360 is capable of rapidly transferring an accumulated block of data to flash memory data card 310 through controller 320. For this reason secondary low power RAM buffer 380 will not normally need to have a storage capacity as large at that of low power RAM buffer 360. But in the interest of having adequate storage capacity, it is recommended that secondary low power RAM buffer 380 also have at least the same storage capacity as primary low power RAM buffer 360. In ATA protocol interface applications this is at least five hundred twelve (512) bytes of storage. Both low power RAM buffer 360 and secondary low power RAM buffer 380 may be volatile memory.

The ATA protocol interface requires that data be written to flash memory data card 310 in blocks of five hundred twelve (512) bytes at a time. It is clear, however, that the present invention is not limited to the ATA protocol interface. The present invention is capable of operating on data blocks that are smaller or larger than 512 bytes in size. In an alternate embodiment of the invention capable of operating on a data block larger than 512 bytes, the size of the storage capacity of low power RAM buffer 360 and secondary low power RAM buffer 380 are selected to contain at least the largest data block to be transferred.

In another alternate embodiment of the present invention, controller 320 stores incoming data in low power RAM buffer 360 for a selected period of time. The predetermined amount of incoming data is chosen to be the data that arrives within that selected period of time. With an internal clock (not shown) controller 320 records how much time has elapsed since the beginning of the selected period of time. When the selected period of time has ended, all data received by controller 320 and stored in low power RAM buffer 360 is transferred to flash memory data card 310. This also includes instances where no data was received during the selected period of time.

Figure 9:
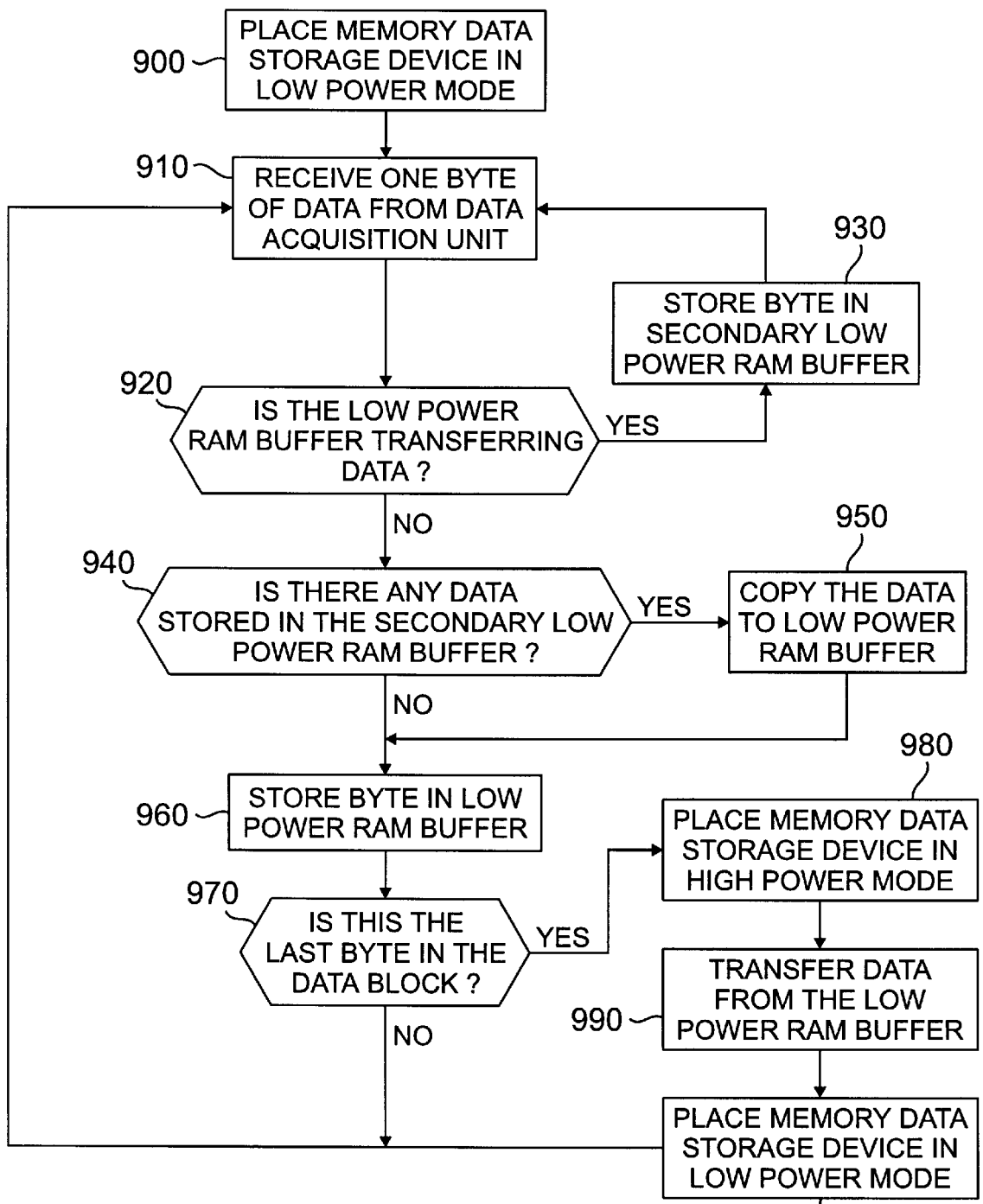
FIG. 9 is a flow diagram illustrating the logic of the operation of the apparatus of the present invention.

FIG. 9 is a flow diagram illustrating the operation of flash memory data storage system 300 according to one embodiment of the present invention. In operation step 900 controller 320 places memory data storage device 310 (e.g., flash memory data card 310) in a low power mode. In operation step 910 controller 320 receives one byte of data from data acquisition unit 340. In decision step 920 a determination is made whether low power RAM buffer 360 is transferring data to memory data storage device 310. If it is, then controller 320 stores the byte of data in secondary low power RAM buffer 380 in operation step 930 and waits to receive the next byte of data in operation step 910.

If low power RAM buffer 360 is not transferring data to memory data storage device 310, then a determination is made in decision step 940 whether there is any data stored in secondary low power RAM buffer 380. If there is, controller 320 in operation step 950 copies the data from secondary low power RAM buffer 380 to low power RAM buffer 360. In operation step 960, controller 320 stores the byte of data in low power RAM buffer 360. If there is no data in secondary low power RAM buffer 380, then controller 320 goes directly from decision step 940 to operation step 960.

In decision step 970 a determination is made whether the byte of data is the last byte in the data block. If it is not, then controller 320 waits to receive the next byte of data in operation step 910. If the byte of data is the last byte of data in the data block, then controller 320 in operation step 980 places memory data storage device 310 in high power mode, and in operation step 990 transfers all of the bytes of data in the data block from low power RAM buffer 360 to memory data storage device 310. After all of the bytes of data in the data block have been transferred to memory data storage device 310, controller 320 in operation step 1000 places the memory data storage device 310 in low power mode and waits to receive the next byte of data in operation step 910.

Because controller 320 is receiving the bytes of data in operation step 910 at a particular data rate, it is possible that controller 320 will receive one or more bytes of data while operation step 990 is in progress. The bytes of data that are received while operation step 990 is in progress are stored in the secondary low power RAM buffer 380 as indicated in operation step 930 until operation step 990 is completed.

The improvement that the present invention provides can be illustrated by comparing the value of the average current required to write one block of 512 bytes of data using the prior art flash memory data storage system with the value of the average current required to write the same size block of data utilizing the flash memory data storage system of the present invention. Table 1 shows results obtained using a prior art flash memory data storage system at a sample frequency of 400 Hz. Table 2 shows the results obtained using a flash memory data storage system of the present invention at the sample frequency of 400 Hz.

TABLE 1

| Prior Art Flash Memory System | Active Current (mA) | Inactive Current (mA) | Active Time (msec) | Inactive Time (msec) | Average Current (mA) |
|---|---|---|---|---|---|
| Write Data to CompactFlash ™ Data Card | 45 | 0.02 | 1277.5 | 0.5 | 44.91 |
| Read Analog Data | 1.18 | 0.01 | 0.036 | 2.5 | 0.027 |
| Quiescent System Power | | | | | 0.5 |
| TOTALS | | | | | 45.43 |

TABLE 2

| Invention Flash Memory System | Active Current (mA) | Inactive Current (mA) | Active Time (msec) | Inactive Time (msec) | Average Current (mA) |
|---|---|---|---|---|---|
| Read from RAM Buffer and Write to CompactFlash ™ Data Card | 70 | 0.02 | 30 | 1280 | 1.66 |
| Read Analog Data | 1.18 | 0.01 | 0.036 | 2.5 | 0.027 |
| Write Data to RAM Buffer | 25 | 0.1 | 0.04 | 2.5 | 0.5 |
| Quiescent System Power | | | | | 0.5 |
| TOTALS | | | | | 2.68 |

A comparison of Table 1 and Table 2 shows that while the prior art flash memory data storage system consumes an average current of 45.43 mA during the time required to read 512 byte data block, the flash memory data storage system of the present invention consumes only an average current of 2.68 mA to do the same task. The flash memory data storage system of the present invention provided a 94% reduction in the average current required to write a 512 byte data block. This percentage is calculated as follows:

$$\text{Percentage}(\%) = \frac{(45.43\text{mA} - 2.68\text{mA})}{45.43\text{mA}} \times (100\%)$$

Table 3 sets forth a comparison showing how much longer certain types of batteries can operate using the flash memory data storage system of the present invention than those same batteries can operate using the prior art flash memory data storage system.

TABLE 3

| Battery | Capacity (mA Hours) | Battery Life Prior Art (days) | Battery Life Invention (days) |
|---|---|---|---|
| Two double A (2 AA) | 2100 | 1.92 | 32.6 |
| One double A (1 AA) | 840 | 0.77 | 13.1 |
| Lithium (CareTech) | 781 | 0.72 | 12.14 |
| Lithium (D12450) | 550 | 0.50 | 8.55 |

The information tabulated in Table 3 illustrates the magnitude of the improvement in battery life that the present invention provides. Although the capacity of each battery (expressed in milliamp-hours) is the same in both flash memory data storage systems, the battery life of each battery is significantly longer when the battery is utilized in the flash memory data storage system of the present invention. This is because the flash memory data storage system of the present invention utilizes battery power in a much more economic manner during the acquisition and recording of electronic data.

These results demonstrate that the present invention has achieved its object of providing an improved electronic data storage system in which the power consumption of the electronic data storage system is reduced compared to the power consumption of prior art electronic data storage systems. Accordingly, the present invention has achieved its object of providing a significant reduction in the power consumption of physiological condition monitors that utilize electronic data storage systems.

Flash memory data storage system 300 is capable of providing improvement in the performance of battery type power supplies that are capable of being recharged. For example, rechargeable batteries that are connected to solar cells may be recharged by electrical current that is provided by the solar cells. Such devices may be used to power a data storage system. Flash memory data storage system 300 is capable of reducing the power consumption in those types of systems in the manner previously described.

Flash memory data storage system 300 may be utilized in a number of different types of electronic data storage systems. For example, it may be utilized in a computer system such as a personal computer, laptop computer, personal digital assistant (PDA), MP3 audio player, etc. Memory data storage device 310 may be a computer hard disk with which the present invention interfaces directly through interface 330. Flash memory data storage system 300 can similarly interface directly with any type of electronic data storage device that utilizes the PC Card ATA protocol. It can also interface directly with devices that use a protocol in which the data blocks to be transferred are larger than 512 bytes or are smaller than 512 bytes. It may also be utilized in wireless messaging devices such as cellular telephones, pagers, wireless devices for receiving Internet service, etc.

Flash memory data storage system 300 may also be utilized in smart appliances. Smart appliances are electric and/or electronic appliances that possess computerized electronic circuitry for monitoring and controlling the operation of the appliance. It may also be utilized in industrial electronic control circuitry including circuitry that is used in the construction and operation of robots and robotic machines.

Flash memory data storage system 300 enables monitor unit 100 of the physiological condition monitor of the present invention to efficiently collect and store data concerning the physiological condition of a person. As shown in FIG. 3, flash memory data card 310 receives and stores data from respiration detector 345 and electrocardiograph detector 355. Flash memory data card 310 may be physically removed from monitor unit 100. A person seeking to access the data stored in flash memory data card 310 simply removes it from monitor unit 100 and places it into a PCMCIA slot in a computer (not shown) or into a PCMCIA slot 220 in base station unit 200. For the CompactFlash™ card it will be necessary to use a CompactFlash™ to PCMCIA adapter. The data on flash memory data card 310 can then be accessed through the computer (not shown) into which the flash memory data card 310 has been inserted or through the base station unit 200 into which the flash memory data card 310 has been inserted.

Figure 4:
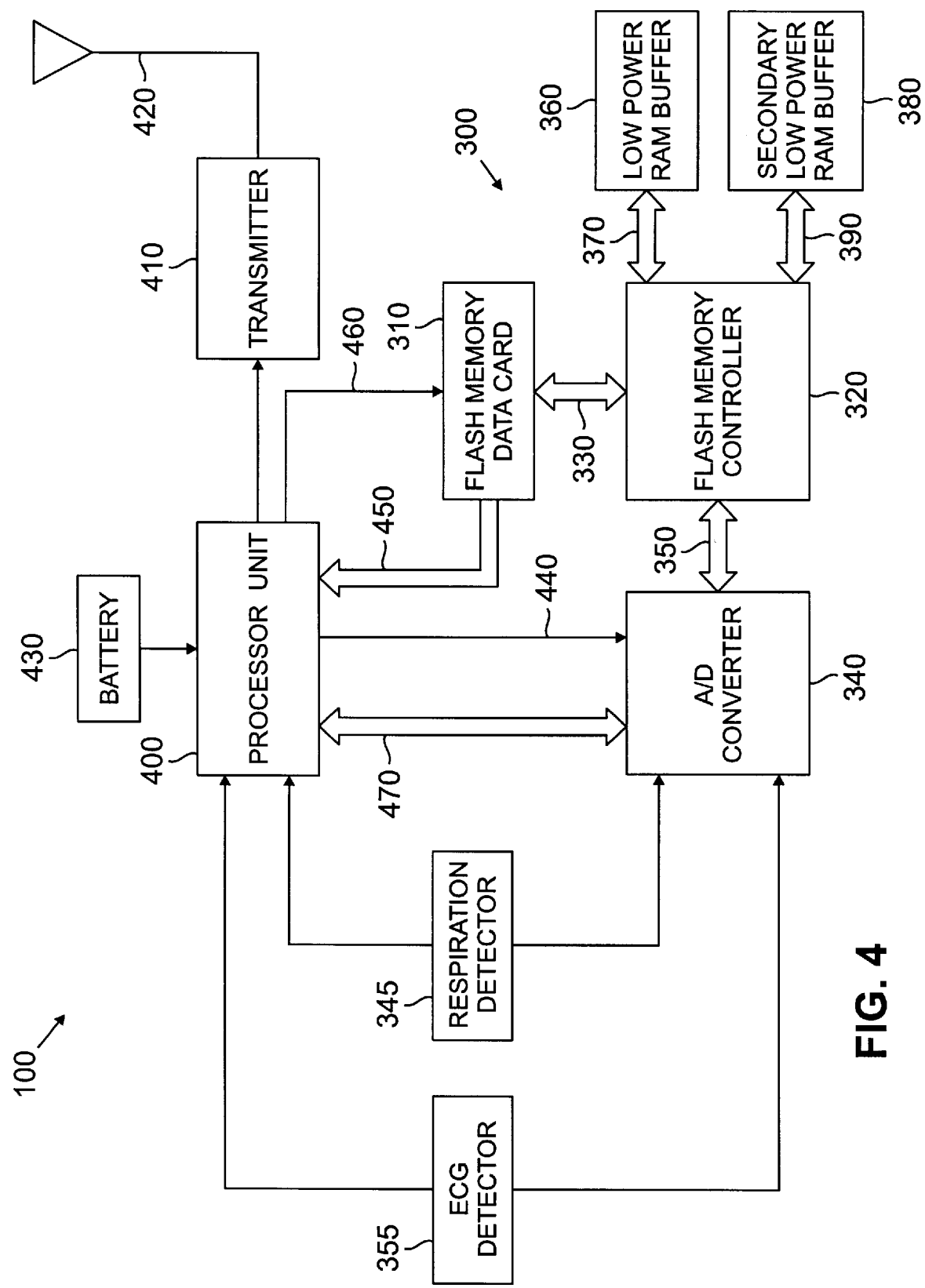
FIG. 4 is a block diagram of an alternate embodiment of the monitor unit of the present invention showing the interconnection of a processor unit and a transmitter with the components of a flash memory data storage system utilizing the present invention.

FIG. 4 shows a block diagram of an alternate embodiment of monitor unit 100 of the present invention. In the alternate embodiment, processor unit 400 is coupled to respiration detector 345 and to electrocardiograph detector 355 and is capable of receiving analog data signals directly from those detectors. Processor unit is also coupled to radio frequency transmitter 410 which is in turn coupled to antenna 420. Processor unit 400 is capable of receiving analog data signals from respiration detector 345 and electrocardiograph detector 355 and causing radio frequency transmitter 410 to transmit those signals to base station unit 200 via transmitter 420.

Battery 430 is coupled to processor unit 400 and is capable of supplying electrical power for the operation of processor unit 400. Although battery 430 is shown coupled only to processor unit 400 in FIG. 4, battery 430 is connected to and provides power to all components of monitor unit 100 through other electrical connections (not shown).

In this alternate embodiment of the present invention, processor unit 400 is capable of operating in a mode in which it sends analog data signals directly from the detectors, 345 and 355, to base station unit 200 via transmitter 410 and antenna 420. In this alternate embodiment of the present invention, base station unit 200 must be capable of converting the analog signals into digital form when it receives the data. Such an embodiment of base station unit 200 will be described below with reference to FIG. 6. In this mode of operation, no data is being actively stored in flash memory data storage system 300. During this mode of operation, flash memory data storage system 300 retains whatever data was previously stored within it.

This mode of operation is utilized whenever the operator of the physiological condition monitor desires to record the data directly at base station unit 200 and conserve the storage capacity of flash memory data storage system 300. Processor unit 400 is capable of selectively enabling the operation of flash memory data storage system 300 in accordance with pre-programmed instructions. Processor unit 400 enables the operation of flash memory data storage system 300 by enabling the operation of data acquisition unit 340 by sending an enabling signal on control line 440.

As shown in FIG. 4, processor unit 400 is coupled to flash memory data storage system 300. Specifically, processor unit 400 is coupled to flash memory data card 310 via interface 450 and control line 460. When flash memory data card 310 is nearly full, it sends a signal to processor unit 400 informing processor unit 400 of that fact. In response, processor unit 400 is capable of sending a signal to flash memory data card 310 via control line 460 to cause flash memory data card 310 to transfer its data to processor unit 400 via interface 450. Processor unit 400 then causes the data to be transmitted to base station unit 200 via transmitter 410 and antenna 420. The data is transmitted in digital form because that is the form in which the data was stored in flash memory data card 310.

Alternatively, in accordance with one or more pre-programmed instructions, processor unit 400 can send a signal to flash memory data card 310 at any time via control line 460 to cause flash memory data card 310 to transfer to processor unit 400 whatever data flash memory data card 310 has stored within it.

In an alternate embodiment of the present invention, processor unit 400 is also coupled to analog to digital converter 340 via interface 470. Processor unit 400 is capable of receiving digital data signals directly from analog to digital converter 340 that contain data from respiration detector 345 and ECG detector 355. Processor unit 400 is capable of sending a signal to analog to digital converter 340 via control line 440 to cause analog to digital converter 340 to transfer its digital data signals to processor unit 400 via interface 470. Processor unit 400 then causes radio frequency transmitter 410 to transmit the digital data signals to base station unit 200 via transmitter 420.

Figure 5:
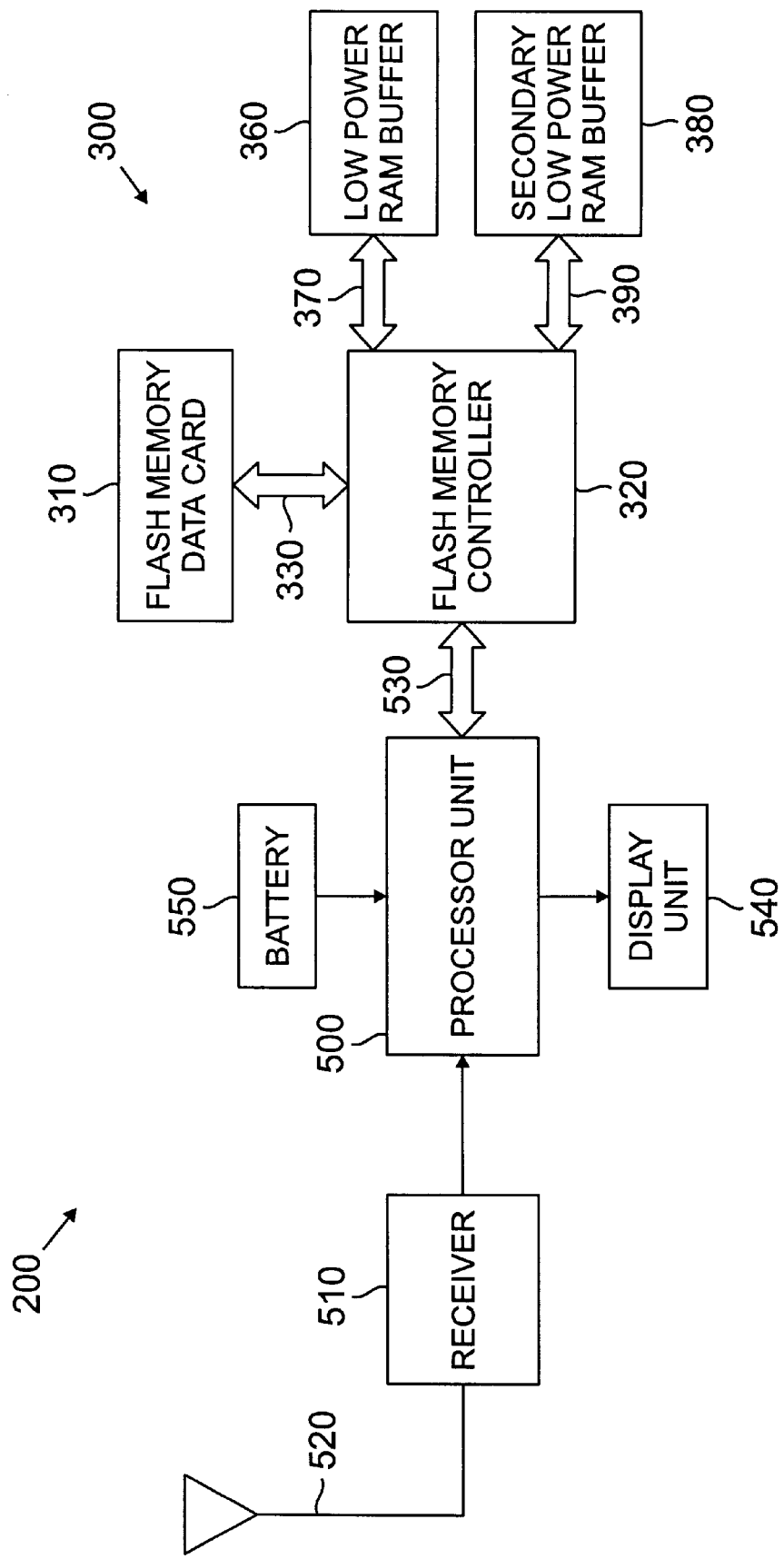
FIG. 5 is a block diagram of one embodiment of the base station unit of the present invention showing the interconnection of the components of a flash memory data storage system utilizing the present invention.

FIG. 5 shows a block diagram of one embodiment of base station unit 200 of the present invention. In this embodiment, processor unit 500 is coupled to radio frequency receiver 510 which in turn is coupled to antenna 520. Processor unit 500 is capable of receiving data signals in digital form directly from receiver 510 via transmitter 520. Processor unit 500 is also coupled to flash memory data storage system 300 via interface 530. Processor unit 500 is also coupled to a display unit 540 and is capable of displaying information on display unit 540 concerning the status of operations of processor unit 500 or the content of data stored in flash memory data card 310. Display unit 540 may be a computer monitor, or LED indicators, or any other type of display unit. Processor unit 500 is also coupled to a keyboard (not shown) or other similar device for communicating instructions to processor unit 500.

Battery 550 is coupled to processor unit 500 and is capable of supplying electrical power for the operation of processor unit 500. Although battery 550 is shown coupled only to processor unit 500 in FIG. 5, battery 550 is connected to and provides power to all components of base station unit 200 through other electrical connections (not shown).

Processor unit 500 is capable of transferring data in digital form directly to flash memory controller 320 via interface 530. The transferred data is stored in flash memory data card 310 in accordance with the method previously described. The data stored in flash memory data card 310 can be accessed by processor unit 500 for display on display unit 540.

Flash memory data card 310 may be physically removed from base station unit 200. A person seeking to access the data stored in flash memory data card 310 in a location other than that of base station unit 200 simply removes flash memory data card 310 from base station unit 200 and places it into a PCMCIA slot in a computer (not shown). For the CompactFlash™ card it will be necessary to use a CompactFlash™ to PCMCIA adapter. The data on flash memory data card 310 can then be accessed through the computer (not shown) into which the flash memory data card 310 has been inserted.

Figure 6:
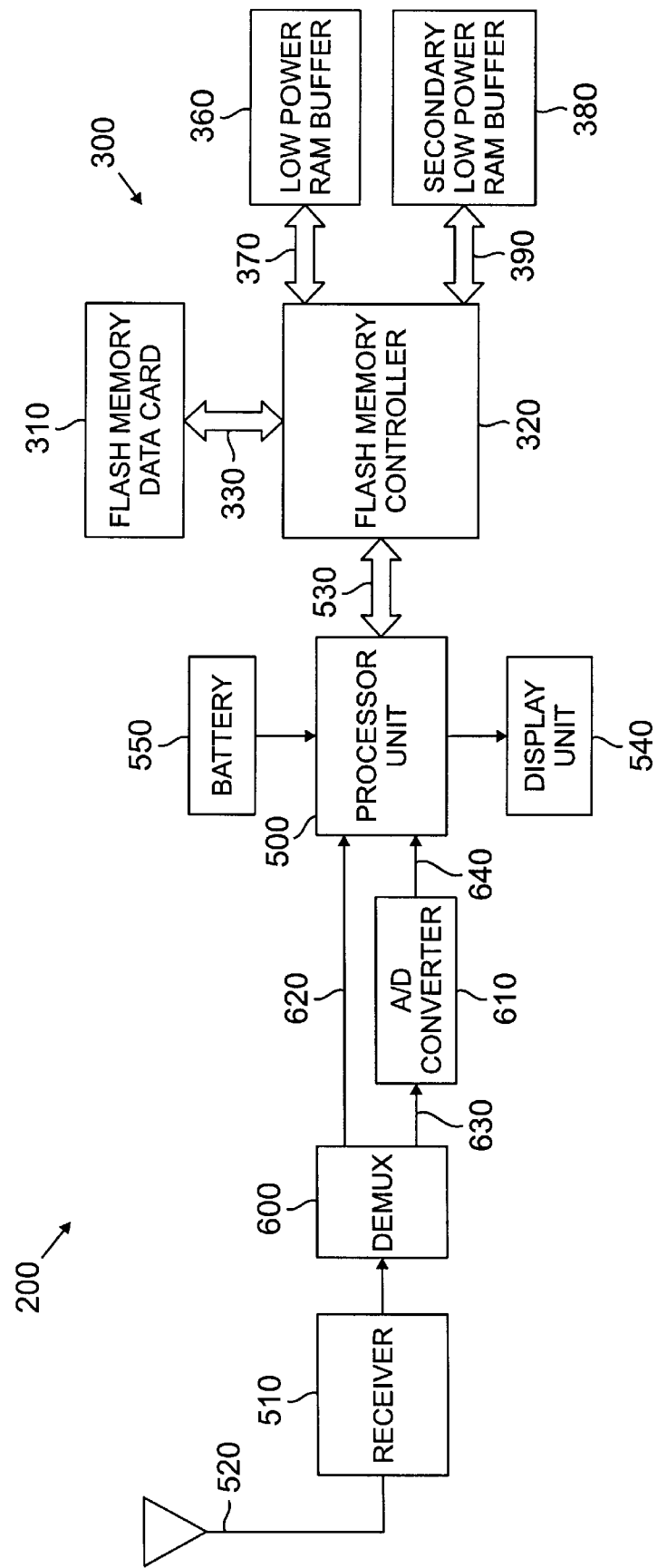
FIG. 6 is a block diagram of an alternate embodiment of the base station unit of the present invention showing the interconnection of a demultiplexer and an analog to digital converter with the components of a flash memory data storage system utilizing the present invention.

FIG. 6 shows a block diagram of an alternate embodiment of base station unit 200. The embodiment of base station 200 shown in FIG. 5 is capable of receiving signals in digital form. The embodiment of base station unit 200 shown in FIG. 6 is capable of receiving signals in both analog and digital form. As shown in FIG. 6, demultiplexer 600 is coupled between receiver 510 and processor unit 500. An analog to digital converter 610 is coupled between demultiplexer 600 and processor unit 500.

Demultiplexer 600 receives either analog signals or digital signals from receiver 510. Demultiplexer 600 is capable of determining which type of signal it has received. If it has received digital signals, then demultiplexer 600 sends them directly to processor unit 500 via signal line 620. If it has received analog signals, then demultiplexer 600 sends them to analog to digital converter 610 via signal line 630. After analog to digital converter 610 has converted the analog signals to digital signals, it then sends them to processor unit 500 via signal line 640. In this embodiment of the invention, base station unit 200 is capable of receiving either type of signal from monitor unit 100.

The present invention may also be used to provide a significant reduction in the power consumption of battery operated flash memory data storage systems in physiological condition monitors that monitor the movement and position orientation of a body. A physiological condition monitor that monitors the movement and position orientation of a body is described in U.S. patent application Ser. No. 09/396,991 filed Sep. 15, 1999 by Lehrman et al. entitled "Systems for Evaluating Movement of a Body and Methods of Operating the Same." U.S. patent application Ser. No. 09/396,991 is hereby incorporated herein by reference for all purposes.

Figure 10:
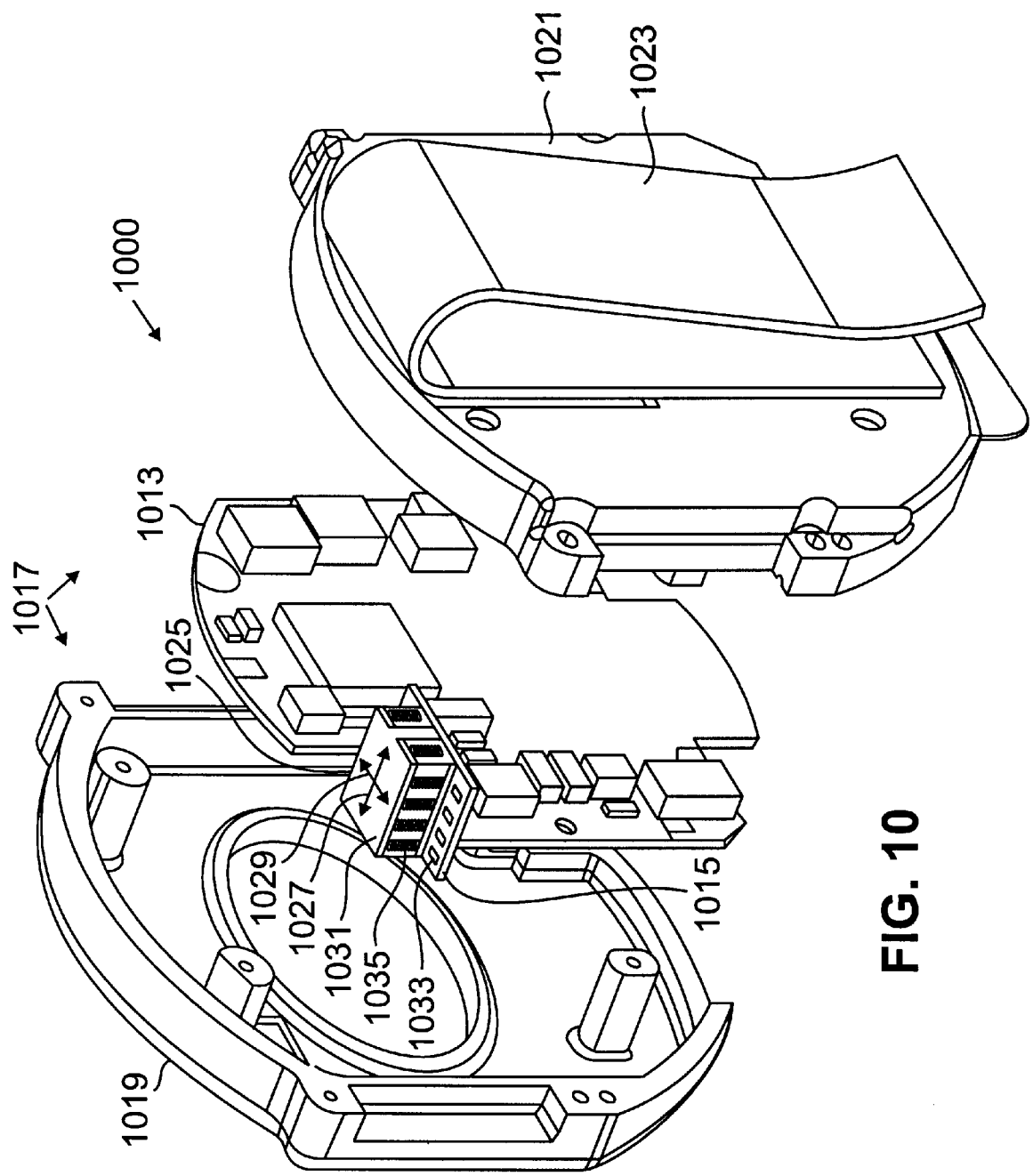
FIG. 10 is an exploded perspective view of a physiological condition monitor for obtaining data relating to the movement and the position orientation of a body.

FIG. 10 is an exploded perspective view of physiological condition monitor 1000 for obtaining data relating to the movement and the position orientation of a body. Monitor 1000 measures and distinguishes selected accelerative events of a body (not shown). As used in this disclosure, the phrases "accelerative events" or "accelerative phenomena" are defined as occurrences of change in velocity of the body (or acceleration), whether in magnitude, direction or both.

Monitor 1000 includes circuit boards 1013 and 1015 (connected boards at right angles to one another) that are associated with a housing (generally designated 1017) utilizing known mounting techniques. Exemplary housing 1017 (and monitor 1000, for that matter), when assembled, is approximately one centimeter thick and is approximately five centimeters across in any direction.

Housing 1017 may comprise, for example, exemplary housing halves 1019 and 1021 that encase boards 1013 and 1015, although those skilled in the art will understand that any configuration suitable for a particular implementation of the invention may be arranged.

Exemplary rear half 1021, is provided with a clip 1023 for associating monitor 10000 with the body (e.g., people, animals, objects of various sorts, etc.). Exemplary clip 1023 is shown as a mechanical spring-type clip, but could be any known attachment device or system, including either mechanical or chemical attachment systems, or any other suitable means for associating monitor 1000 with the body.

Monitor 1000 includes a processor (shown in FIG. 11) and a sensor 1025. Exemplary sensor 1025 operates to sense accelerative phenomena of the body, and is mounted on circuit board 1013 with x and y axes 1027 and 1029, respectively, oriented thereat (though other orientations could be utilized).

Sensor 1025 is illustratively shown as a plural-axis (dual shown) acceleration measuring device suitably mounted on a single monolithic integrated circuit (one conventional sensor is an accelerometer available from Analog Devices, Inc., located at One Technology Way, Norwood, Mass., United States of America, namely, Model No. ADXL202). Sensor 1025 includes polysilicon surface-micromachined sensor layer 1031 built on top of silicon wafer 1033. Polysilicon springs 1035 resiliently suspend sensor layer 1031 over the surface of wafer 1033 providing resistance against acceleration forces. Deflection of the sensor layer is measured using a differential capacitor formed by independent fixed and central plates, the fixed plates driven by 180° out of phase square waves having amplitude proportional to acceleration. Signal outputs from each axis of sensor 1025 are conditioned (i.e., phase sensitive demodulation and low pass filtering) and presented at analog output nodes. While not utilized in the primary advantageous embodiment of this invention, the Analog Devices' accelerometer is operable to convert the analog signals to duty cycle modulated ("DCM") signals at a DCM stage providing digital output signals capable of being directly counted at a processor.

While techniques for reconstructing analog signals from the digital output signals may suitably be utilized (e.g., passing the duty cycle signals though an RC filter), thereby allowing use of the digital signal output of a sensor of monitor 1000 hereof. Use of the analog signal outputs has been found advantageous due to the increased bandwidth availability (0.01 Hz to 5 kHz, adjustable at capacitors at the output nodes to bandlimit the nodes implementing low-pass filtering for antialiasing and noise reduction), and thus measuring sensitivity, attained. A typical noise floor of 500 $\mu$g/Hz is achieved, thereby allowing signals below 5 mg to be resolved for bandwidths below 60 Hz.

According to the illustrated embodiment, sensor 1025 generates analog output voltage signals corresponding to measurements in the x and y axes, which include both an ac voltage component proportional to G forces (i.e., dynamic acceleration component related to vibrations of sensor layer 1031) and a dc voltage component proportional to an angle relative to earth (i.e., static acceleration component related to gravity). This open loop acceleration measurement architecture, capable of measuring both static and dynamic acceleration, can thus be utilized to determine position of a body by measuring both the x and y output voltages simultaneously, as well as measure forces of impact experienced by a body. This information comprises state indicia, and utilizing both signal components from both outputs, the sensed accelerative phenomena of the body may subsequently be processed to distinguish a variety of accelerative phenomena and, ultimately, to selectively act based on the distinctions, as is described in detail hereafter to determine whether the evaluated body movement is normal or abnormal, and, if abnormal, whether the same is within tolerance.

It is noted that the foregoing embodiment has been introduced for illustrative purposes only. In alternate embodiments, any sensor that is capable of sensing accelerative phenomena relative to a body may be used in lieu of, or even in conjunction with, sensor 1025. Further, alternate orientations of sensor 1025 may be used for different applications.

Figure 11:
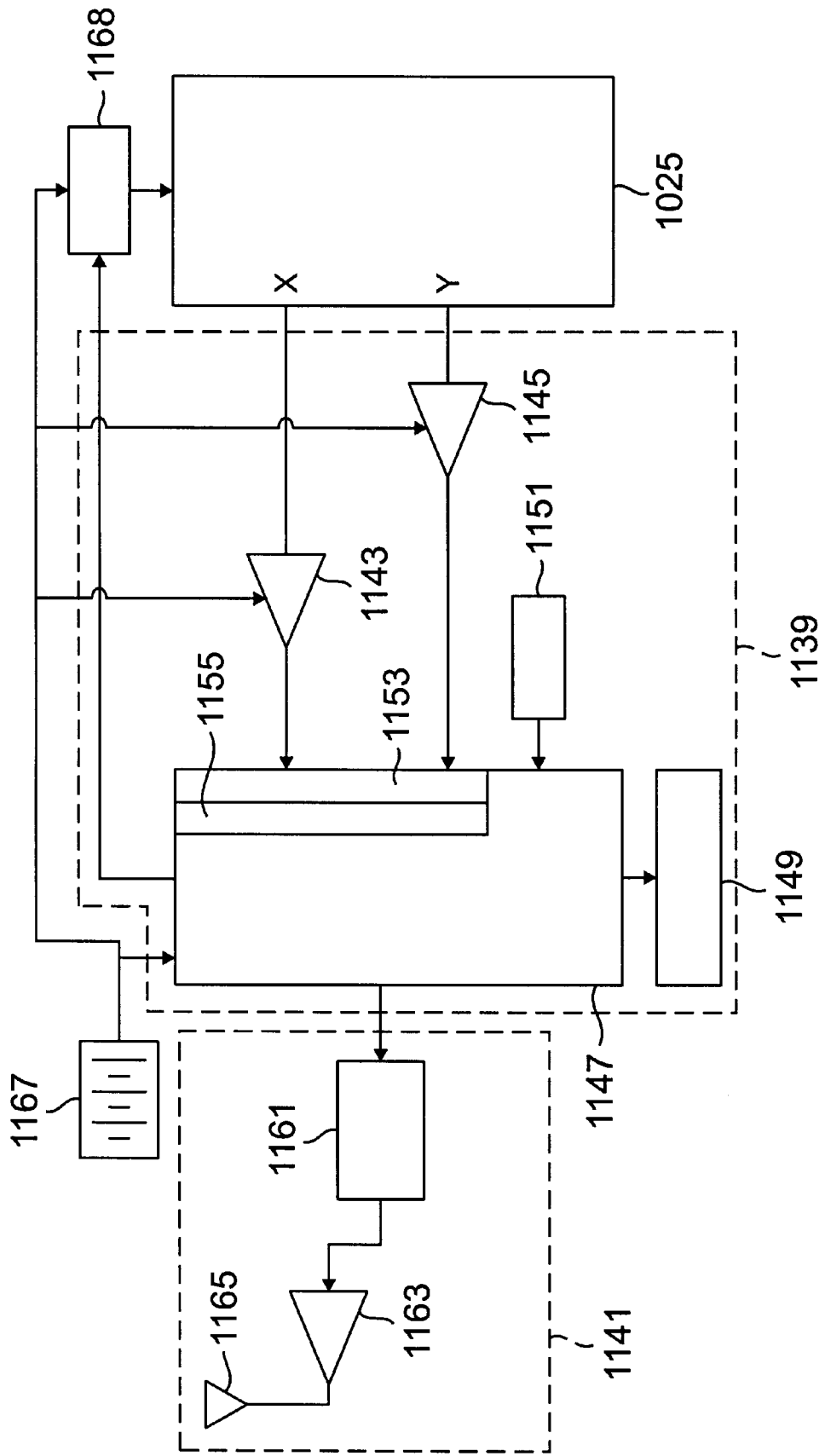
FIG. 11 is a block diagram of one embodiment of the physiological condition monitor shown in FIG. 10 showing the interconnection of the monitor components.

FIG. 11 is a block diagram of one embodiment of physiological condition monitor 1000 showing the interconnection of the monitor components. The illustrated embodiment includes processing circuitry 1139, indicating circuit 1141, power supply 1167, and a switch 1168, along with sensor 1025.

Exemplary processing circuitry 1139 illustratively includes a processor 1147 and buffer amplifiers 1143 and 1145 that buffer the analog x and y outputs from sensor 1025. Exemplary processor 1147, which is associated with sensor 1025, is capable of processing the sensed accelerative phenomena as a function of at least one accelerative event characteristic to thereby determine whether an evaluated body movement is within environmental tolerance. Processor 1147 also preferably generates state indicia while processing the sensed accelerative phenomena, which may represent the state of the body within the environment over time. Processor 1147 is associated with a crystal oscillator/clock 1149, switch (DIP) inputs 1151, an analog-digital conversion circuitry 1153 and a DSP filter 1155 (one conventional processor is available from Texas Instruments, Inc., located in Dallas, Tex., United States of America, namely, Model No. MSP430P325).

Exemplary indicating circuit 1141, in response to direction from processor 1147, is operable to at least one of initiate an alarm event; communicate such state, or tolerance, indicia to a monitoring controller; generate statistics; etc. Indicating circuit 1141 may take any number of forms, however, for use in monitor 1000 of one advantageous embodiment, stage 1141 is an RF transmitter including RF modulator 1161 enabled by processor 1147. Exemplary data is presented and modulated at modulator 1161, amplified at amplifier 1163 and transmitted at antenna 1165 (to a remote receiver unit as discussed hereinafter).

According to the present embodiment, power for the various components of monitor 1000 is provided by power supply 1167, which illustratively is a conventional 3.6 volt battery. Low power management may suitably be under the control of processor 1147 utilizing exemplary switched/power supply voltage FET switch 1168 at sensor 1025, which provides power only during sampling cycles, and operates to shut components down during non-use cycles. For instance, processor 1147 may be taken off-line when processing is complete, reducing current drain.

It should be noted that the various circuitry discussed heretofore has been introduced herein for illustrative purposes only. Monitor 1000 may be implemented using any suitably arranged computer or other processing system including micro, personal, mini, mainframe or super computers, as well as network combinations of two or more of the same. In point of fact, in one advantageous embodiment, sensor 1025 and processor 1147 are not co-located, but rather associated wirelessly. To that end, the principles of the present invention may be implemented in any appropriately arranged device having processing circuitry. Processing circuitry may include one or more conventional processors, programmable logic devices, such as programmable array logic ("PALs") and programmable logic arrays ("PLAs"), digital signal processors ("DSPs"), field programmable gate arrays ("FPGAs"), application specific integrated circuits ("ASICs"), large scale integrated circuits ("LSIs"), very large scale integrated circuits ("VLSIs") or the like, to form the various types of circuitry, processors, controllers or systems described and claimed herein.

A detailed description of the method of operation of monitor 1000 is set forth in previously referenced U.S. patent application Ser. No. 09/396,991 filed Sep. 15, 1999 by Lehrman et al. entitled "Systems for Evaluating Movement of a Body and Methods of Operating the Same."

Figure 12:
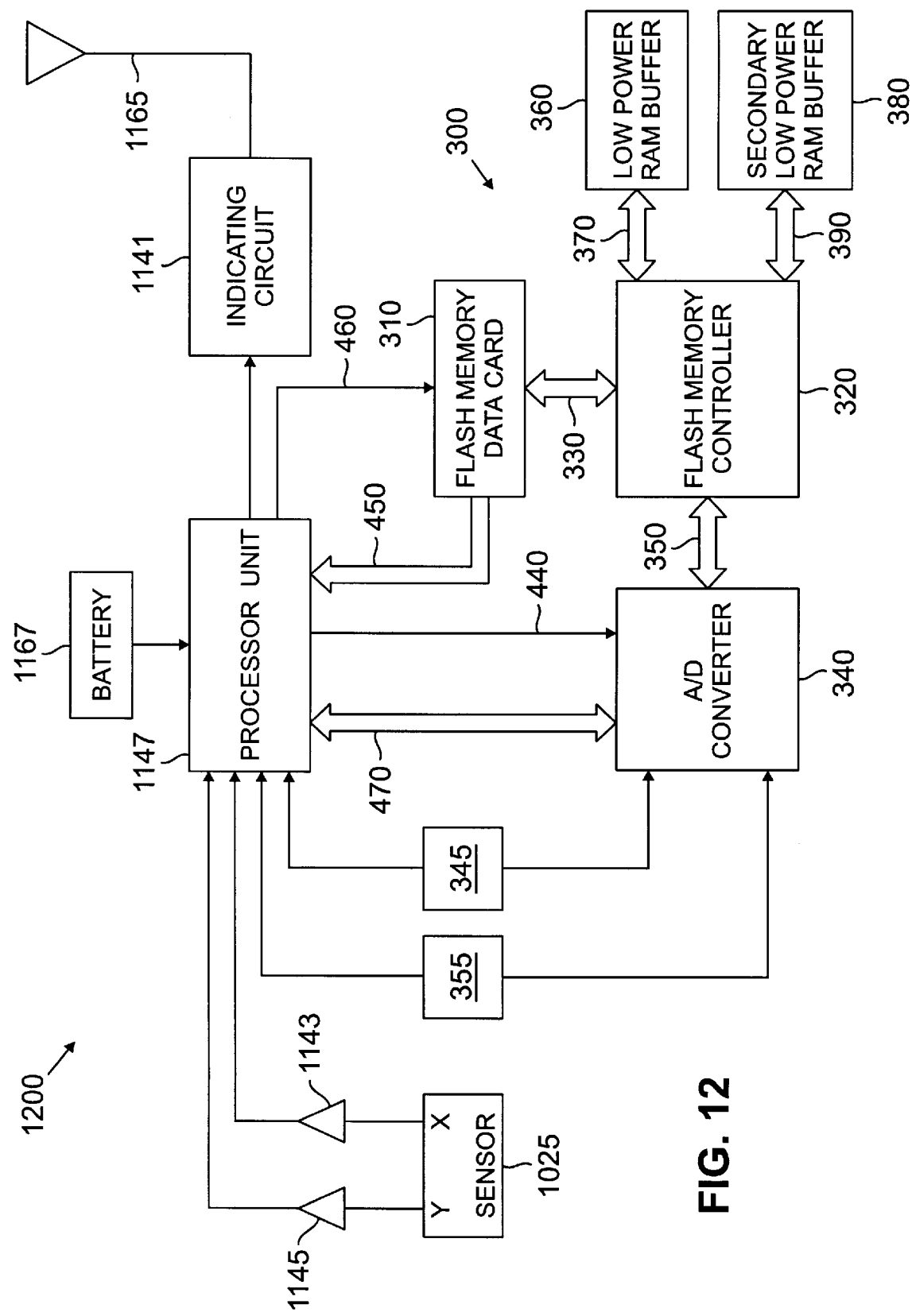
FIG. 12 is a block diagram of one embodiment of a physiological condition monitor for obtaining data relating to the movement and the position orientation of a body utilizing the present invention.

FIG. 12 is a block diagram of one embodiment of physiological condition monitor 1000 utilizing the present invention for reducing power consumption. This particular exemplary embodiment 1200 shows sensor 1025 coupled to processor 1147 via buffer amplifier 1143 and buffer amplifier 1145. Although battery 1167 is shown coupled only to processor 1147, it is actually is coupled to and supplies electrical power to all of the other components in embodiment 1200 via other electrical connections (not shown). For convenience, antenna 1165 has been shown separately from indicating circuit 1141.

Movement and position data from sensor 1025 may be stored in flash memory data system 300 in accordance with the principles that have previously been described. Specifically, processor 1147 is coupled to analog to digital converter 340 via interface 470. Processor 1147 is capable of sending movement and position data signals from sensor 1025 directly to analog to digital converter 340 which, in this case, serves as the data acquisition device for flash memory data storage system 300. Processor 1147 is capable of sending a control signal to analog to digital converter 340 via control line 440 to cause analog to digital converter 340 to store the data signals that processor 1147 transfers via interface 470.

Alternatively, the movement and position data from sensor 1025 may be transmitted via indicating circuit 1141 and antenna 1165 to a base station unit 200. If the movement and position data is in digital form, then the base station unit 200 described with reference to FIG. 5 may be utilized. If the movement and position data is in analog form, then the base station unit 200 described with reference to FIG. 6 may be utilized.

As shown in FIG. 12, sensor 1025 may be coupled to processor 1147 along with other physiological condition monitors such as ECG detector 355 and respiration detector 345. Other types of physiological condition monitors may also be utilized concurrently. In this manner different types of data may be collected simultaneously for the purpose of facilitating subsequent studies to correlate the data.

Although the present invention has been described in detail, those skilled in the art should understand that they can make various changes, substitutions and alterations herein without departing from the spirit and scope of the invention in its broadest form.

What is claimed is:

1. An apparatus capable of monitoring at least one physiological condition of a person in which data about said at least one physiological condition is stored in a memory data storage device, said apparatus comprising:

a memory data storage device capable of operating in a high power mode when data is being written to said memory data storage device and capable of operating in a low power mode when inactive;

a plurality of detectors capable of being coupled to said person, said plurality of detectors comprising at least one detector capable of obtaining data about at least one physiological condition of said person;

a data acquisition device coupled to said plurality of detectors capable of receiving from at least one detector incoming data to be written to said memory data storage device;

a controller coupled to said memory data storage device capable of writing data to said memory data storage device and coupled to said data acquisition device capable of receiving incoming data from said data acquisition device; and a first low power buffer coupled to said controller, wherein said controller stores said incoming data in said first low power buffer until a predetermined amount of incoming data has been accumulated in said first low power buffer and wherein said controller transfers said accumulated predetermined amount of incoming data to said memory data storage device in a single data transfer.

2. The apparatus as set forth in claim 1 wherein said predetermined amount of incoming data is determined by a size of said predetermined amount of incoming data.

3. The apparatus as set forth in claim 2 wherein said size of said predetermined amount of incoming data is five hundred twelve bytes of data.

4. The apparatus as set forth in claim 1 wherein said predetermined amount of incoming data is determined by a selected time duration during which said incoming data has been accumulated.

5. The apparatus as set forth in claim 1 wherein said controller transfers said accumulated predetermined amount of incoming data to said memory data storage device when said memory data storage device is in said high power mode.

6. The apparatus as set forth in claim 1 further comprising a second low power buffer coupled to said controller capable of storing said incoming data when said accumulated predetermined amount of incoming data is being transferred from said first low power buffer to said memory data storage device.

7. The apparatus as set forth in claim 1 wherein said memory data storage device is of a battery powered type having a relatively high power consumption when data is written to said memory data storage device.

8. The apparatus as set forth in claim 1 wherein said memory data storage device is a flash memory card.

9. The apparatus as set forth in claim 1 wherein said data acquisition device is an analog to digital converter capable of converting data from said plurality of detectors from an analog form of data to a digital form of data.

10. The apparatus as set forth in claim 1 wherein one of said plurality of detectors is a respiration detector.

11. The apparatus as set forth in claim 1 wherein one of said plurality of detectors is an electrocardiograph detector.

12. The apparatus as set forth in claim 1 comprising a processor unit coupled to said plurality of detectors, said processor unit capable of receiving data from said plurality of detectors; and a transmitter coupled to said processor unit capable of transmitting from said processor unit to a base station said data from said plurality of detectors.

13. The apparatus as set forth in claim 12 wherein said processor is coupled to said data acquisition device and wherein said processor is capable of selectively enabling the operation of said data acquisition device.

14. The apparatus as set forth in claim 1 comprising a processor unit coupled to said memory data storage device, said processor unit capable of receiving data from said memory data storage device; and a transmitter coupled to said processor unit capable of transmitting data from said processor unit to a base station.

15. The apparatus as set forth in claim 14 wherein said processor is capable of causing said data from said memory data storage device to be transmitted to said base station by said transmitter.

16. An apparatus capable of receiving a signal representative of at least one physiological condition of a person in which data about said signal is stored in a memory data storage device, the apparatus comprising:

a memory data storage device capable of operating in a high power mode when data is being written to said memory data storage device and capable of operating in a low power mode when inactive;

a receiver capable of being coupled to an antenna and capable of receiving a signal representative of at least one physiological condition of a person;

a processor unit coupled to said receiver capable of receiving incoming data in the form of a signal representative of at least one physiological condition of a person and capable of writing said incoming data to said memory data storage device;

a controller coupled to said memory data storage device and capable of writing to said memory data storage device and coupled to said processor unit and capable of receiving said incoming data from said processor unit; and a first low power buffer coupled to said controller, wherein said controller stores said incoming data in said first low power buffer until a predetermined amount of incoming data has been accumulated in said first low power buffer and wherein said controller transfers said accumulated predetermined amount of incoming data to said memory data storage device in a single data transfer.

17. The apparatus as set forth in claim 16 wherein said predetermined amount of incoming data is determined by a size of said predetermined amount of incoming data.

18. The apparatus as set forth in claim 17 wherein said size of said predetermined amount of incoming data is five hundred twelve bytes of data.

19. The apparatus as set forth in claim 16 wherein said predetermined amount of incoming data is determined by a selected time duration during which said incoming data has been accumulated.

20. The apparatus as set forth in claim 16 wherein said controller transfers said accumulated predetermined amount of incoming data to said memory data storage device when said memory data storage device is in said high power mode.

21. The apparatus as set forth in claim 16 further comprising a second low power buffer coupled to said controller capable of storing said incoming data when said accumulated predetermined amount of incoming data is being transferred from said first low power buffer to said memory data storage device.

22. The apparatus as set forth in claim 16 wherein said memory data storage device is of a battery powered type having a relatively high power consumption when data is written to said memory data storage device.

23. The apparatus as set forth in claim 16 wherein said memory data storage device is a flash memory card.

24. The apparatus as set forth in claim 16 wherein said signal representative of a physiological condition of a person is a signal representative of said person's respiration.

25. The apparatus as set forth in claim 16 wherein said signal representative of a physiological condition of a person is a signal representative of said person's cardiac function.

26. The apparatus as set forth in claim 16 comprising
a demultiplexer coupled to said receiver capable of receiving from said receiver both analog signals and digital signals;
an analog to digital converter coupled to said demultiplexer capable of converting analog signals received by said demultiplexer to digital signals; and
wherein said processor unit is coupled to said demultiplexer and is coupled to said analog to digital converter and is capable of receiving incoming data in the form of digital signals representative of at least one physiological condition of a person and is capable of writing said incoming data to said memory data storage device.

27. A method of reducing power consumption in an electronic data storage system in a physiological condition monitor comprising the steps of:
placing a memory data storage device in a physiological condition monitor in a low power mode of operation;
storing data in a first low power buffer when said memory data storage device is in a low power mode of operation until a predetermined amount of data has been stored in said first low power buffer;
placing said memory data storage device in a high power mode of operation; and
transferring said predetermined amount of data to said memory data storage device when said memory data storage device is in a high power mode of operation.

28. A method as claimed in claim 27 together with the step of:
storing other data in a second low power buffer when said first low power buffer is transferring said predetermined amount of data to said memory data storage device; and
transferring said other data to said first low power buffer when said first low power buffer has completed the transfer of said predetermined amount of data to said memory data storage device.

29. A method of reducing power consumption in a flash memory data storage system in a physiological condition monitor comprising the steps of:
placing a flash memory data card in a physiological condition monitor in a low power mode of operation;
storing data in a first low power buffer when said flash memory data card is in a low power mode of operation until a specified amount of data has been stored in said first low power buffer;
placing said flash memory data card in a high power mode of operation; and
transferring said specified amount of data to said flash memory data card when said flash memory data card is in a high power mode of operation.

30. A method as claimed in claim 29 together with the step of:
storing other data in a second low power buffer when said first low power buffer is transferring said specified amount of data to said flash memory data card; and
transferring said other data to said first low power buffer when said first low power buffer has completed the transfer of said specified amount of data to said flash memory data card.

31. An apparatus capable of evaluating movement of a body relative to an environment, said apparatus comprising:
a sensor, associable with said body, that senses accelerative phenomena of said body;
a processor, associated with said sensor, that processes said sensed accelerative phenomena as a function of at least one accelerative event characteristic to thereby determine whether said evaluated body movement is within environmental tolerance;
a memory data storage device capable of operating in a high power mode when data is being written to said memory data storage device and capable of operating in a low power mode when inactive;
a data acquisition device coupled to said processor capable of receiving from said processor incoming data from said sensor to be written to said memory data storage device;
a controller coupled to said memory data storage device capable of writing data to said memory data storage device and coupled to said data acquisition device capable of receiving incoming data from said data acquisition device; and
a first low power buffer coupled to said controller, wherein said controller stores said incoming data in said first low power buffer until a predetermined amount of incoming data has been accumulated in said first low power buffer and wherein said controller transfers said accumulated predetermined amount of incoming data to said memory data storage device in a single data transfer.

32. An apparatus as set forth in claim 31 wherein said controller transfers said accumulated predetermined amount of incoming data to said memory data storage device when said memory data storage device is in said high power mode.

33. An apparatus as set forth in claim 31 further comprising a second low power buffer coupled to said controller capable of storing said incoming data when said accumulated predetermined amount of incoming data is being transferred from said first low power buffer to said memory data storage.

34. An apparatus as set forth in claim 31 wherein said predetermined amount of incoming data is determined by a size of said predetermined amount of incoming data.

35. An apparatus as set forth in claim 31 wherein said memory data storage device is a flash memory data card.

36. An apparatus as set forth in claim 31 further comprising a plurality of detectors coupled to said body, said plurality of detectors comprising at least one detector capable of obtaining data about at least one physiological condition of said body.

37. An apparatus as set forth in claim 31 further comprising a transmitter coupled to said processor capable of transmitting from said processor to a base station data that has been acquired by said apparatus.

38. An apparatus as set forth in claim 35 wherein said at least one physiological condition of said body is selected from the list of respiration activity, cardiac activity, level of blood glucose, level of blood oxygenation, movement of a body, and position orientation of a body.

39. A method of reducing power consumption in an electronic data storage system in an apparatus capable of evaluating movement of a body relative to an environment of the type comprising:
a sensor, associable with said body, that senses accelerative phenomena of said body;
a processor, associated with said sensor, that processes said sensed accelerative phenomena as a function of at least one accelerative event characteristic to thereby determine whether said evaluated body movement is within environmental tolerance;

a memory data storage device capable of operating in a high power mode when data is being written to said memory data storage device and capable of operating in a low power mode when inactive;

a data acquisition device coupled to said processor capable of receiving from said processor incoming data from said sensor to be written to said memory data storage device;

a controller coupled to said memory data storage device capable of writing data to said memory data storage device and coupled to said data acquisition device capable of receiving incoming data from said data acquisition device; and a first low power buffer coupled to said controller, wherein said controller stores said incoming data in said first low power buffer until a predetermined amount of incoming data has been accumulated in said first low power buffer and wherein said controller transfers said accumulated predetermined amount of incoming data to said memory data storage device in a single data transfer, wherein said method comprises the steps of:

placing said memory data storage device is a low power mode of operation;

storing data in said first low power buffer when said memory data storage device is in a low power mode of operation until a predetermined amount of data has been stored in said first low power buffer;

placing said memory data storage device in a high power mode of operation; and transferring said predetermined amount of data to said memory data storage device when said memory data storage device is in a high power mode of operation.

40. A method as claimed in claim 39 together with the step of:

storing other data in a second low power buffer when said first low power buffer is transferring said predetermined amount of data to said memory data storage device; and transferring said other data to said first low power buffer when said first low power buffer has completed the transfer of said predetermined amount of data to said memory data storage device.

\* \* \* \* \*